US008000446B2

(12) United States Patent
Van Woezik

(10) Patent No.: US 8,000,446 B2
(45) Date of Patent: Aug. 16, 2011

(54) X-RAY EXAMINATION APPARATUS

(75) Inventor: Johannes Theodorus Maria Van Woezik, Helenaveen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 92 days.

(21) Appl. No.: 12/374,822

(22) PCT Filed: Oct. 12, 2006

(86) PCT No.: PCT/IB2006/053749
§ 371 (c)(1),
(2), (4) Date: Jan. 23, 2009

(87) PCT Pub. No.: WO2007/046041
PCT Pub. Date: Apr. 26, 2007

(65) Prior Publication Data
US 2010/0002844 A1    Jan. 7, 2010

(30) Foreign Application Priority Data
Oct. 19, 2005   (EP) .................................. 05109713

(51) Int. Cl.
*H05G 1/02*   (2006.01)
(52) U.S. Cl. ........................ 378/98.2; 378/198
(58) Field of Classification Search .................. 378/198, 378/98, 98.2
See application file for complete search history.

(56) References Cited

U.S. PATENT DOCUMENTS

| 5,627,873 A | * | 5/1997 | Hanover et al. ............... 378/197 |
| 5,901,200 A | * | 5/1999 | Krause .......................... 378/198 |
| 5,967,982 A | * | 10/1999 | Barnett ......................... 600/429 |
| 6,007,243 A | * | 12/1999 | Ergun et al. ................... 378/197 |
| 6,149,592 A | * | 11/2000 | Yanof et al. ................... 600/427 |
| 6,256,374 B1 | * | 7/2001 | Tomasetti et al. ............ 378/98.2 |
| 6,431,751 B1 | * | 8/2002 | Everett et al. ................. 378/197 |
| 6,844,865 B2 | * | 1/2005 | Stasko .......................... 345/1.3 |
| 7,016,454 B2 | * | 3/2006 | Warnberg ........................ 378/9 |

(Continued)

FOREIGN PATENT DOCUMENTS
DE    29510803 U1    11/1995
(Continued)

OTHER PUBLICATIONS

BAYTEK, Designer Monitors, 2000, http://www.baytek.de/englisch/Designer.htm, on May 26, 2005, 16:00, Bangalore Time.

(Continued)

*Primary Examiner* — Edward J Glick
*Assistant Examiner* — Thomas R Artman

(57) ABSTRACT

An X-ray examination apparatus (100) is described, comprising a mobile carriage (10) carrying a human-operable control input device (21) and a display device (22), the carriage (10) having a front side (11) and a back side (12); wherein said human-operable control input device is located closer to the front side (11) of the carriage while said display device is located closer to the back side (12) of the carriage; wherein the carriage has a control position where the said display device has its image screen (23) directed substantially towards the front side (11) of the carriage, and a surgeon position where the said display device has its image screen (23) directed substantially towards the back side (12) of the carriage; and wherein said display device is mounted to the mobile carriage such as to be displaceable between the control position and the surgeon position.

11 Claims, 4 Drawing Sheets

U.S. PATENT DOCUMENTS

| | | | |
|---|---|---|---|
| 7,250,922 B2 * | 7/2007 | Sakaniwa | 345/1.3 |
| 2003/0233040 A1 | 12/2003 | Sakaniwa | |

FOREIGN PATENT DOCUMENTS

| | | |
|---|---|---|
| DE | 19625407 A1 | 1/1998 |
| DE | 20118841 U1 | 5/2003 |
| EP | 0231969 A1 | 8/1987 |
| EP | 1113354 A2 | 7/2001 |
| JP | 2004313739 A | 11/2004 |
| JP | 2005037747 A | 2/2005 |
| KR | 2004000847 A | 1/2004 |
| WO | 0024234 A | 4/2000 |

OTHER PUBLICATIONS

LCD MONITORARM, Flat Panel Arms from Spacedec, 2005, http://www.lcdmonitorarm.com/lcd_arm_3.htm, on May 26, 2005, 16:30, Bangalore Time.

* cited by examiner

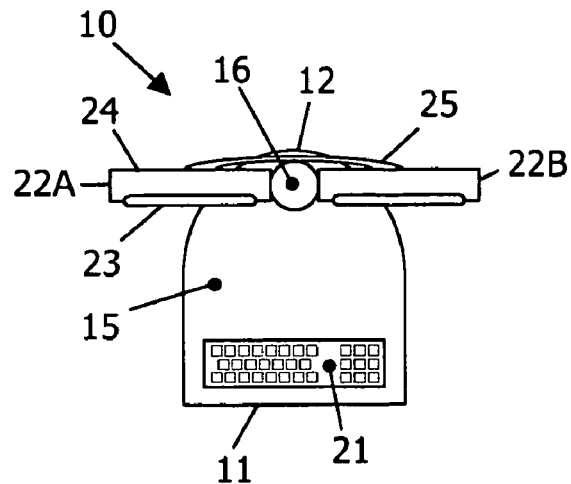
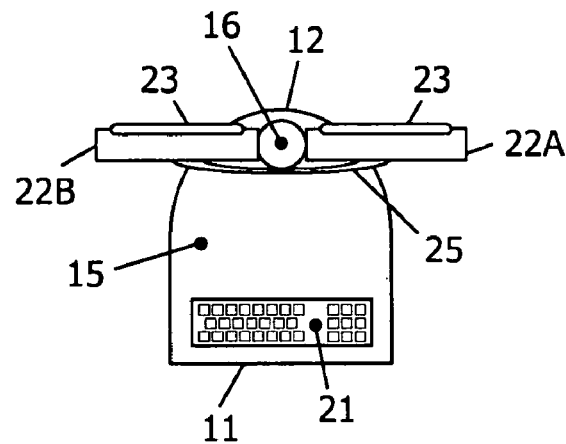
FIG. 2A    FIG. 2B
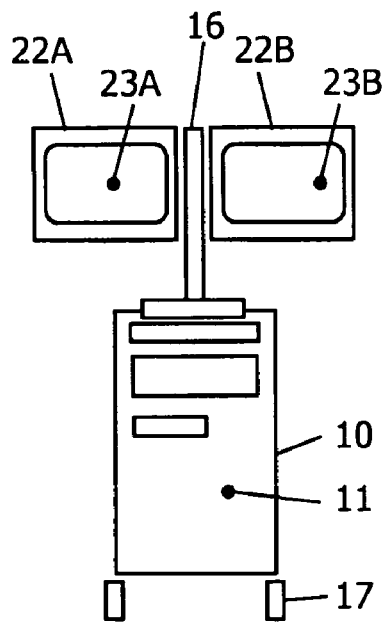
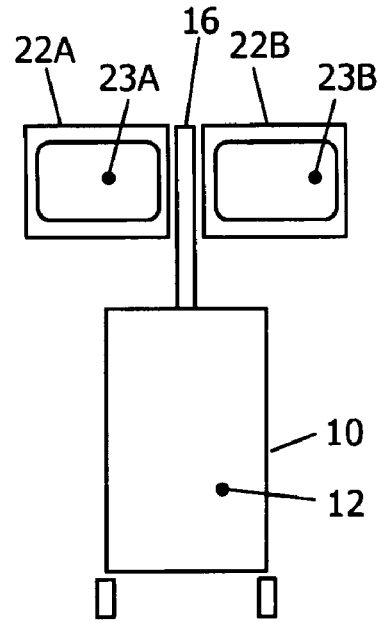
FIG. 2C    FIG. 2D

X-RAY EXAMINATION APPARATUS

FIELD OF THE INVENTION

The present invention relates in general to an X-ray examination apparatus, i.e. an apparatus for examining a patient (human or animal) by X-ray imaging. More specifically, the present invention relates to a mobile X-ray examination apparatus, but the scope of the present invention is not limited to a mobile apparatus.

BACKGROUND OF THE INVENTION

An X-ray examination apparatus comprises in general a source for generating an X-ray beam, means for directing the beam towards a target (i.e. patient), receiver means for receiving X-ray radiation that has passed the target, and imaging means for processing the receiver signals and calculating X-ray images. Since the above-specified components are already known, while the present invention does not relate to improving the above-specified components, and while further the present invention can be implemented with existing components as specified above, it is not necessary here to explain in further detail the design and operation of the above-specified components.

An X-ray examination apparatus further comprises control means, for controlling the setting and operation of the apparatus, and display means for displaying the X-ray image. Typically, the control means comprise one or more buttons, one or more keyboards, etc, and the display means comprise at least one display device, for instance implemented as a CRT monitor, an LCD monitor, or the like. Since such control means and display means are already known per se, while the present invention does not relate to improving the control means or display means, and while further the present invention can be implemented with known per se control means and display means, it is not necessary here to explain in further detail the design and operation of the control means and display means.

Usually, the control means and display means are located at some distance from the X-ray source and receiver means, being mutually coupled by cables. This applies specifically to mobile apparatus, designed for being used in an operating theatre. While performing a surgical operation, a surgeon may wish to have X-ray images of the operation field; this applies for instance in the case of an instrument being advanced in a blood vessel. The X-ray source and receiver means must necessarily be located relatively close to the patient, the control means must be located close to an operator, and the display means should preferably be located close to the surgeon. On the other hand, when the surgeon does not need the support by X-ray images, the relatively large components of the X-ray apparatus are just an obstacle to the surgeon.

For easy displacement, the control means and display means are typically arranged on a mobile carriage, that can be wheeled towards the surgeon if needed, and that can be wheeled away if not needed.

Now a practical problem is that, in order to be of use to the surgeon, the display device of the display means must be directed towards the surgeon. On the other hand, if an operator is to control the setting of the apparatus using the control means, he should be able to watch the display device. This means that the operator is positioned at the same side of the display device as the surgeon, but this is very uncomfortable, at least to the surgeon, because in the operating theatre there is typically very little space.

A further practical problem is that the control means (key board and the like) are positioned at the same side of the display device as the operator, and thus are directed towards the operation field. By the very nature of operation proceedings, it is possible that some body fluids are released from the patient and come into contact with the control means. Cleaning the control means, which is of course needed from a hygienic point of view, is relatively difficult. Conversely, the close proximity of the control means, which are difficult to clean, forms a potential risk to the sterility of the operation field.

It is a general objective of the present invention to eliminate or at least reduce the above problems.

SUMMARY OF THE INVENTION

According to an important aspect of the present invention, the display device(s) of the display means is/are mounted to the mobile carriage with a rotation freedom of at least 180° around a vertical axis.

With such feature, it is possible to position the mobile carriage close to the surgeon with the control means directed away from the surgeon; thus, the control means are less susceptible to potential body fluids and do less endanger the sterility of the operation field. An operator, for operating the control means, can then be positioned to the mobile carriage opposite to the surgeon, so the operator does no longer constitute an obstacle to the surgeon. If the operator needs to watch the display device, the display device is turned towards the operator. During surgery, if the surgeon wishes to see the X-ray images, the display device is turned over approximately 180° towards the surgeon.

It is noted that Japanese patent application 2003-276787, publication number 2004-213739, discloses an X-ray imaging apparatus, with image display screens mounted on a carriage, where remote displacement means are provided for slightly displacing the orientation of the display screens. These displacement means comprise an electric motor, a gear, and remote control means for controlling the motor, where the remote control means are operated by the surgeon, for tuning the angle of the display screens such that he can clearly see the image. This is a quite complicated device, and is intended for adjustment of the screen orientation over relatively small angles only. In contrast, according to the present invention, the display device has a rotational freedom over approximately 180°, which is not disclosed in the publication, so that the control means can be positioned opposite from the surgeon, which is also not disclosed in the publication. Although the present invention does not necessarily exclude the use of a remote controlled motor for rotating the display device, the display device is preferably freely rotatable around the vertical axis, so that it can easily and rapidly be rotated by hand.

BRIEF DESCRIPTION OF THE DRAWINGS

These and other aspects, features and advantages of the present invention will be further explained by the following description with reference to the drawings, in which same reference numerals indicate same or similar parts, and in which:

FIG. 2A is a schematic top view of a carriage with two display devices in a control position;

FIG. 2B is a schematic top view of the carriage with two display devices in a surgeon position;

FIG. 2C is a schematic front side view of the mobile carriage in its control position;

FIG. 2D is a schematic back side view of the mobile carriage in its surgeon position;

DETAILED DESCRIPTION OF THE INVENTION

Figure 1:
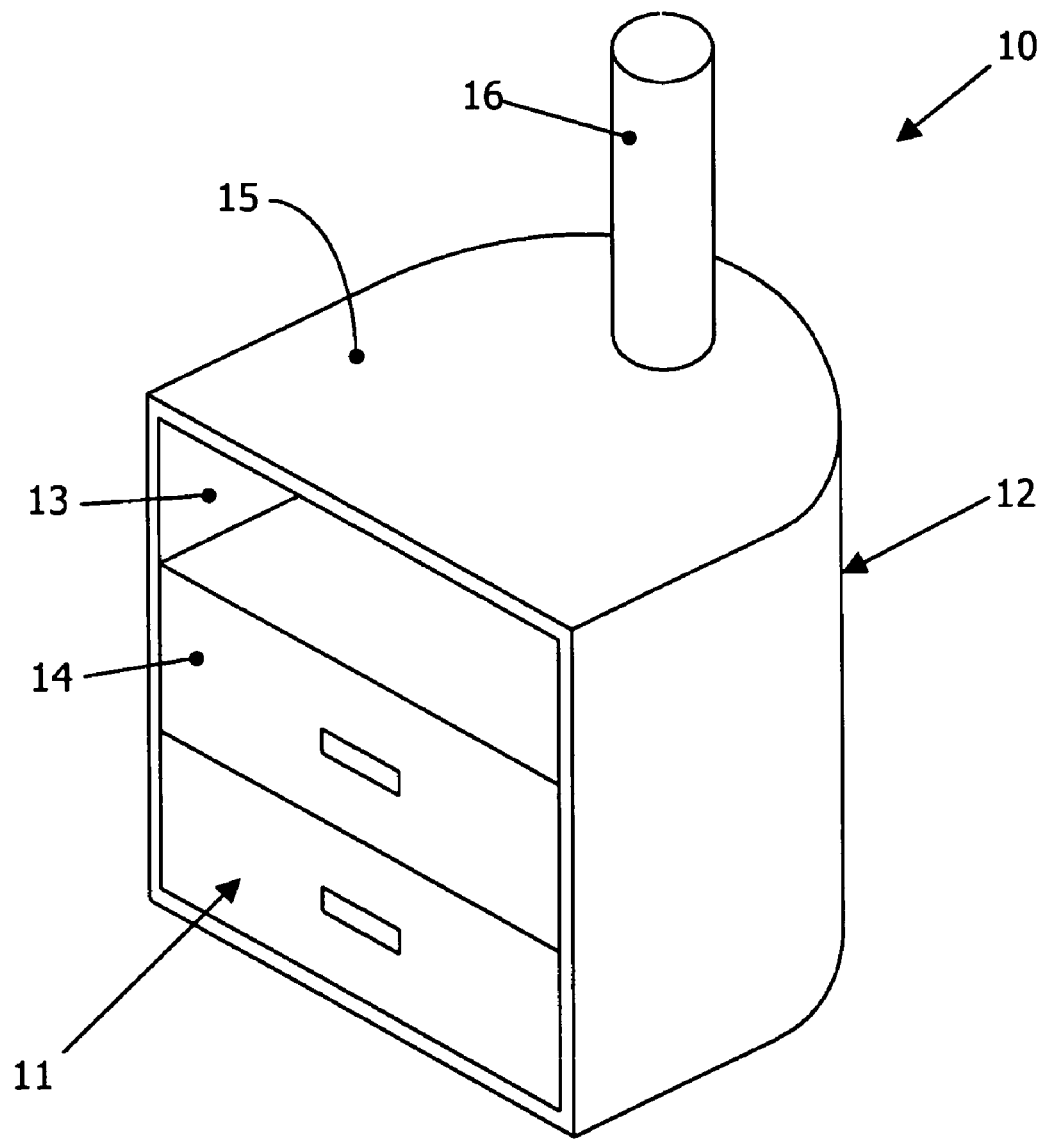
FIG. 1 schematically shows a perspective view of a mobile carriage for an X-ray examination apparatus.

FIG. 1 schematically shows a perspective view of a mobile carriage 10 for an X-ray examination apparatus, with a front side 11 and a back side 12 opposite the front side 11. The back side 12 preferably has a smooth, easy to clean surface. The front side may give access to a storage space 13, a drawer 14, etc. The carriage 10 typically has wheels 17 (see FIGS. 2C and 2D), but these are not shown in FIG. 1. A top surface is indicated at 15. At a position close to the back side 12, the carriage 10 has a mounting column 16 extending from the top surface 15, for mounting one or more display devices.

FIG. 2A is a schematic top view of the carriage 10, showing a key board 21 arranged on the top surface 15, close to the front side 11. The figure further shows two display devices 22, distinguished from each other by the addition of character A and B, mounted to the column 16. It is noted that the present invention also relates to embodiments having only one display device, or having three or more display devices. In the embodiment as shown, the two display devices 22A, 22B are mounted on opposite sides of the column 16, substantially at the same height. It is, however, also possible to have screens at different heights.

It is noted that the display device is shown as a flat screen device, which is preferred, indeed, but not essential.

Each display device 22 has an image screen 23, where the image is displayed, and a back side 24 opposite the image screen 23. The back side 24 preferably has a smooth, easy to clean surface. According to an important aspect of the present invention, the display devices 22A, 22B can be pivoted around the vertical column 16.

FIG. 2A shows the mobile carriage 10 in a control position, wherein the display devices 22 have their image screens 23 directed towards the front side 11 of the carriage. In this control position, an operator (not shown) can take a position at the front side of the carriage 10 and operate the keyboard 21 or other control means located at the front side of the carriage, while at the same time viewing the information displayed on the image screens 23 of the display devices 22. FIG. 2C is a schematic front side view of the mobile carriage 10 in its control position, also showing wheels 17.

FIG. 2B is a view comparable to FIG. 2A, showing the mobile carriage 10 in a surgeon position, wherein the display devices 22 have their image screens 23 directed towards the back side 12 of the carriage. In this surgeon position, a surgeon (not shown) can take a position at the back side of the carriage 10 and perform an operation on a patient while at the same time, if desired, viewing the information displayed on the image screens 23 of the display devices 22. FIG. 2D is a schematic back side view of the mobile carriage 10 in its surgeon position.

Figure 3A:
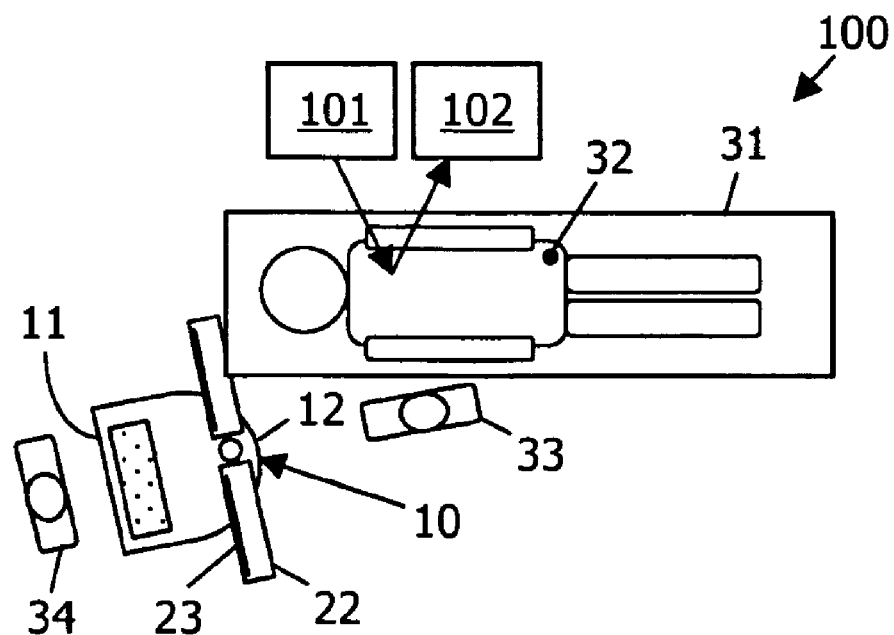
FIG. 3A is a schematic top view of an operation theatre including the mobile carriage according to the present invention in its control position.
Figure 3B:
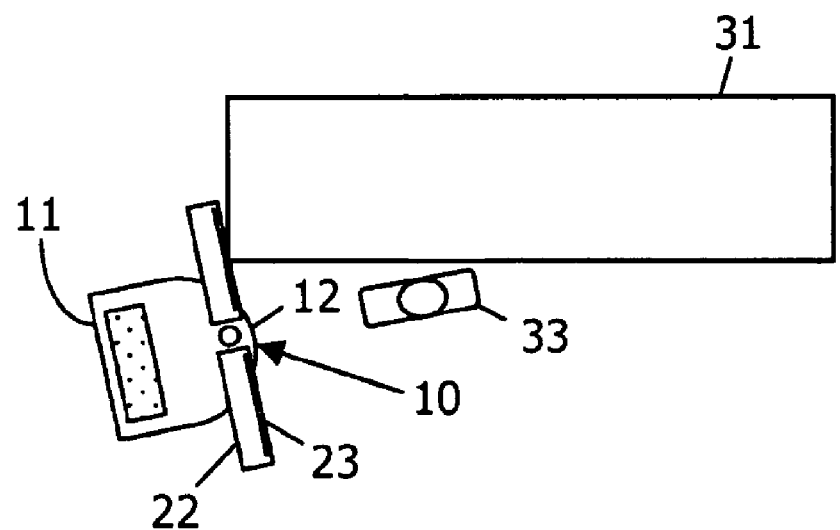
FIG. 3B is a schematic top view comparable to FIG. 3A, showing the mobile carriage in its surgeon position.

FIG. 3A is a schematic top view of an operation theatre, illustrating an operating table 31 for receiving a patient 32, a surgeon 33 positioned besides the table 31. In the operation theatre, an X-ray examination apparatus 100 according to the invention is arranged. This X-ray examination apparatus 100 comprises a source 101 for generating an X-ray beam and for directing the beam towards the patient 32, and receiver means 102 for receiving X-ray radiation that has passed the patient 32; for sake of convenience, the source 101 and the receiver 102 are depicted at the same side of the table 31, opposite the surgeon 33. The X-ray examination apparatus 100 further comprises a mobile carriage 10 as described earlier, arranged besides the surgeon 33, having its back side 12 directed towards the surgeon 32 while an operator 34 is positioned at the front side 11 of the carriage 10. FIG. 3A shows the mobile carriage 10 in its control position, having the image screens 23 directed towards the operator 34. FIG. 3B is a view similar to FIG. 3A, yet showing the mobile carriage 10 in its surgeon position, having the image screens 23 directed towards the surgeon 33.

Apart from being rotatable around a vertical axis, the display devices are preferably also adjustable in the vertical direction, i.e. the height of the display devices can be adjusted. Since means for mounting a screen such that its vertical position is adjustable are known per se, a more detailed description of the design of such mounting means is omitted here.

It is noted that, in case the carriage 10 has two or more display devices, the height of the display devices may be adjustable individually, or the display devices may be moved all at the same time. It is further noted that the display device(s) may be vertically displaced with respect to the column 16, but it is also possible that the column is vertically displaceable with respect to the undercarriage.

It is further noted that, for better visibility by the surgeon, the display devices may be mounted tiltable with respect to a horizontal axis. Since means for mounting a screen such that it can be tilted are known per se, a more detailed description of the design of such mounting means is omitted here.

Regarding the horizontal rotational movement of the display devices, it is preferred that they move together, as an integral body. Therefore, the apparatus preferably comprises coupling means 25 for coupling the display devices together. Such coupling means 25 may be any suitable coupling means, as will be clear to a person skilled in the art; in FIG. 2A, these coupling means 25 are schematically depicted as a bracket.

Figure 4A:
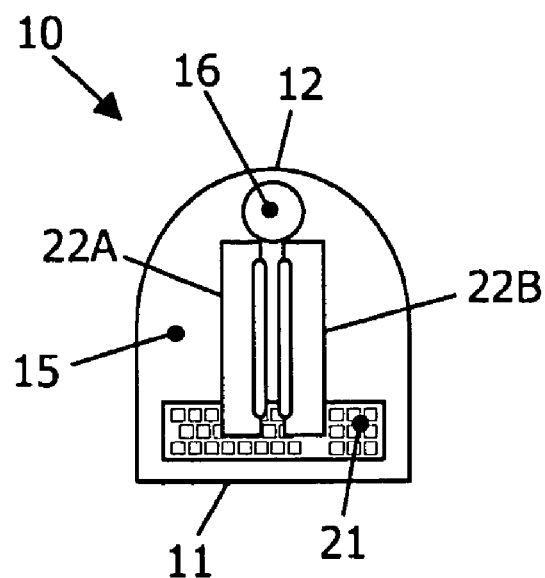
FIG. 4A is a schematic top view comparable to FIG. 2A, showing the mobile carriage in its storage position.
Figure 4B:
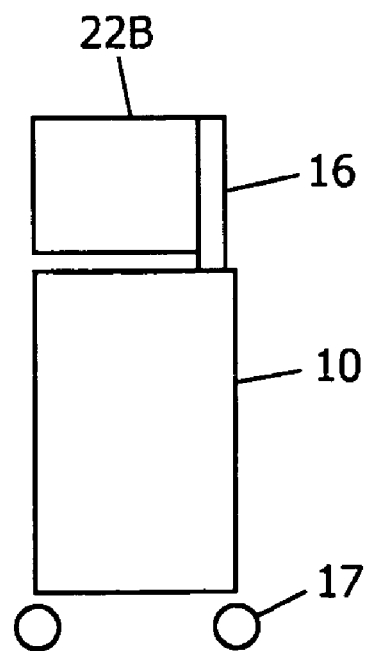
FIG. 4B is a schematic side view comparable to FIG. 2C, showing the mobile carriage in its storage position.

However, in a case where two display devices are mounted next to each other, on opposite sides of a column, the total width of the display devices will typically be larger than the width of the carriage 10, so that the display devices project beyond the carriage and hence are quite vulnerable. In a preferred embodiment, reducing the vulnerability of the screens, the display devices are rotatable individually with respect to the column 16, for instance by removing the coupling means 25. In that case, the display devices can be brought to a storage position by rotating the first display device 22A over an angle of approximately 90° and by rotating the opposite display device 22B in the opposite direction over an angle of approximately 90°, such that the image screens 23 of the display devices 22 are directed towards each other. Then, the display devices 22 will be positioned above the top surface 15 of the carriage 10, within its perimeter. FIG. 4A is a top view comparable to FIG. 2A, illustrating this storage position, and FIG. 4B is a side view comparable to FIG. 2C, illustrating this storage position.

It should be clear to a person skilled in the art that the present invention is not limited to the exemplary embodiments discussed above, but that several variations and modifications are possible within the protective scope of the invention as defined in the appending claims.

For instance, instead of being mounted on a central column, the display device(s) may also be arranged on a platform which is rotatable around a vertical axis.

Further, in the above description it has been explained that the surgeon and the operator can be positioned on opposite sides of the carriage 10. However, it is also possible that the carriage 10 is to be positioned at an oblique position with respect to the operation table, in which case the angular distance between the operator and the surgeon is less than 180°. This angular distance may be as small as 90°. Therefore, the present invention is already embodied in a carriage where the display device(s) is (are) rotatable over at least 90°.

Further, in the above description it has been explained that the display devices are freely rotatable with respect to the carriage. Nevertheless, the display devices may be provided with releasable clamping means for fixing the position of the display devices with respect to the carriage, for increased stability, which clamping means are then released when it is desired to rotate the display devices.

The invention claimed is:

1. X-ray examination apparatus, comprising:
   an X-ray source;
   X-ray receiver means;
   imaging means for calculating X-ray images on the basis of output signals from the receiver means;
   control means for controlling the setting and operation of the apparatus, including at least one human-operable control input device;
   at least two display devices, each display device having an image screen for displaying the X-ray images; and
   a mobile carriage carrying said human-operable control input device and said at least two display devices, the carriage having, a top surface, a front side and a back side,
   wherein said human-operable control input device is located on the top surface closer to the front side of the carriage and said at least two display devices are located closer to the back side of the carriage,
   wherein the carriage has a control position in which each of the said at least two display devices has its image screen directed substantially towards the front side of the carriage, and a surgeon position in which each of the said at least two display devices has its image screen directed substantially towards the back side of the carriage, and
   wherein said at least two display devices alone are mounted to the mobile carriage via a mounting column, on opposite sides of the mounting column, to be freely rotatably displaceable together as an integral body between the control position and the surgeon position, wherein a total width of the display devices together as the integral body is larger than a width of the carriage, wherein the mounting column is located close to the back side of the carriage, extending vertically with respect to the top surface of the carriage, and
   wherein the carriage further has a storage position in which each of the said at least two display devices is freely rotatably displaceable to have its image screen directed substantially towards the other and being positioned above the top surface of the carriage within its perimeter, wherein a first one of said display devices is displaceable from its control position to its storage position by rotation around a vertical axis with respect to the carriage over 90° in a first direction, and wherein the second one of said display devices is displaceable from its control position to its storage position by rotation around said vertical axis with respect to the carriage over 90° in the opposite direction.

2. X-ray examination apparatus according to claim 1, wherein said at least two display devices are freely rotatable around a vertical axis of the mounting column with respect to the carriage.

3. X-ray examination apparatus according to claim 1, wherein said at least two display devices have a rotation freedom of at least 90° around a vertical axis of the mounting column.

4. X-ray examination apparatus according to claim 3, wherein the rotation freedom of said at least two display devices with respect to the carriage includes one selected from the group consisting of 180° and more than 180°.

5. X-ray examination apparatus according to claim 1, wherein the mounting column is fixed to the carriage and the said at least two display devices are rotatable with respect to the mounting column.

6. X-ray examination apparatus according to claim 1, wherein the mounting column is rotatable with respect to the carriage.

7. X-ray examination apparatus according to claim 1, further wherein each of said at least two display devices is vertically displaceable with respect to the carriage.

8. X-ray examination apparatus according to claim 1, wherein each of the said at least two display devices is tiltable with respect to the carriage.

9. X-ray examination apparatus according to claim 1, further comprising coupling means for coupling the at least two display devices such that they are displaced together as the integral body.

10. X-ray examination apparatus according to claim 1, wherein the back side of the carriage comprises a smooth surface, wherein the smooth surface is characterized as an easy to clean surface.

11. Mobile carriage for use in an X-ray examination apparatus, the carriage having a top surface, a front side and a back side, the carriage carrying:
   at least one human-operable control input device and at least two display devices, each display device having an image screen for displaying X-ray images;
   wherein said human-operable control input device is located on the top surface closer to the front side of the carriage and said at least two display devices are located closer to the back side of the carriage;
   wherein the carriage has a control position in which each of the said at least two display devices has its image screen directed substantially towards the front side of the carriage, and a surgeon position in which each of the said at least two display devices has its image screen directed substantially towards the back side of the carriage;
   wherein said at least two display devices alone are mounted to the mobile carriage via a mounting column, on opposite sides of the mounting column, to be freely rotatably displaceable together as an integral body between the control position and the surgeon position, wherein a total width of the display devices together as the integral body is larger than a width of the carriage, wherein the mounting column is located close to the back side of the carriage, extending vertically with respect to the top surface of the carriage; and
   wherein the carriage further has a storage position in which each of the said at least two display devices is freely rotatably displaceable to have its image screen directed substantially towards the other and being positioned above the top surface of the carriage within its perimeter, wherein a first one of said display devices is displaceable from its control position to its storage position by rotation around a vertical axis with respect to the carriage over 90° in a first direction, and wherein the second one of said display devices is displaceable from its control position to its storage position by rotation around said vertical axis with respect to the carriage over 90° in the opposite direction, said at least two display devices being mounted to the mobile carriage to be freely rotatable around a vertical axis of the mounting column with respect to the carriage, the rotational freedom being one selected from the group consisting of at least 90° and at least 180°.

* * * * *